US008837837B2

(12) United States Patent
Rezaee et al.

(10) Patent No.: US 8,837,837 B2
(45) Date of Patent: Sep. 16, 2014

(54) METHODS, APPARATUSES, AND COMPUTER PROGRAM PRODUCTS FOR DETERMINING A MODULATION TRANSFER FUNCTION OF AN IMAGING SYSTEM

(75) Inventors: Mahmoud Ramze Rezaee, Vancouver (CA); Yonas Tesfazghi Weldeselassie, Vancouver (CA)

(73) Assignee: McKesson Financial Holdings, Hamilton (BM)

( * ) Notice: Subject to any disclaimer, the term of this patent is extended or adjusted under 35 U.S.C. 154(b) by 161 days.

(21) Appl. No.: 13/340,869

(22) Filed: Dec. 30, 2011

(65) Prior Publication Data
US 2013/0170719 A1 Jul. 4, 2013

(51) Int. Cl.
*G06K 9/00* (2006.01)
*G06K 9/48* (2006.01)

(52) U.S. Cl.
USPC .......................................... 382/199; 382/131

(58) Field of Classification Search
None
See application file for complete search history.

(56) References Cited

U.S. PATENT DOCUMENTS

| 6,728,003 | B1 | 4/2004 | Gallagher et al. |
| 6,900,884 | B2 | 5/2005 | Alderson et al. |
| 7,783,440 | B1 | 8/2010 | Lewis et al. |
| 2004/0247167 | A1* | 12/2004 | Bueno et al. .................. 382/132 |

OTHER PUBLICATIONS

Evans, Joshua D., et al. "Noise-resolution tradeoffs in x-ray CT imaging: A comparison of penalized alternating minimization and filtered backprojection algorithms." Medical physics 38.3 (2011): 1444.*

Gerber, Thomas C., et al. "Effect of acquisition technique on radiation dose and image quality in multidetector row computed tomography coronary angiography with submillimeter collimation." Investigative radiology 40.8 (2005): 556-563.*

Freedman, Matthew T., Jyh-Shyan Lin, and Seong K. Mun. "Automatic lung nodule detection using profile matching and back-propagation neural network techniques." Journal of Digital Imaging 6.1 (1993): 48-54.*

Razaee, M. R. et al., *A Model for the Modulation Transfer Function of Cardiovascular X-ray Systems*, Investigative Radiology, vol. 31, Mar. 1996, pp. 161-171.

Keat, N., *Comparison of Assessment Techniques for CT Scanner Spatial Resolution Measurement*, ImPACT, St. George's Hospital, CTUG, Jun. 10, 2005, 20 pages.

Edyvean, S. et al., *Gammex RM1 CT Phantom, 438*, Imaging Performance Assessment of CT Scanners, St. Georges Hospital, London, CT Users Oct. 2007, 27 pages.

Phantom Order Form [online] [retrieved Feb. 8, 2012]. Retrieved from the Internet: <URL: http://www.acr.org/accreditation/computed/qc_forms/Phantom_Order_Form.aspx>. 2 pages.

* cited by examiner

*Primary Examiner* — Nirav G Patel
(74) *Attorney, Agent, or Firm* — Alston & Bird LLP

(57) ABSTRACT

Methods, apparatuses, and computer program products are provided for determining a modulation transfer function of an imaging system. A method may include accessing an image of a phantom having a substantially circular shaped feature captured by the imaging system. The method may further include detecting the circular shaped feature within the image. The method may additionally include defining at least one line extending from a point within the detected circular shaped feature to a point outside of the circular shaped feature. The method may also include determining an edge spread function based at least in part on the defined at least one line. The method may further include determining the modulation transfer function of the imaging system based at least in part on the determined edge spread function. Corresponding apparatuses and computer program products are also provided.

18 Claims, 12 Drawing Sheets

METHODS, APPARATUSES, AND COMPUTER PROGRAM PRODUCTS FOR DETERMINING A MODULATION TRANSFER FUNCTION OF AN IMAGING SYSTEM

TECHNOLOGICAL FIELD

Embodiments of the present invention relate generally to imaging technology and, more particularly, to methods, apparatuses, and computer program products for determining a modulation transfer function of an imaging system.

BACKGROUND

The modulation transfer function (MTF) of an imaging system is often used to assess the spatial resolution of the imaging system. In the case of medical imaging systems, which may be used to capture images for diagnosing patient conditions, it may be particularly important for imaging systems to be calibrated appropriately so as to provide a sufficient level of spatial resolution. Accordingly, measurement of the MTF is often used for periodic quality assurance evaluations of medical imaging systems. MTF is also used as a tool to quantify detail loss associated with application of an image processing algorithm to a captured image.

BRIEF SUMMARY OF SOME EXAMPLES OF THE INVENTION

Methods, apparatuses, and computer program products are herein provided for determining a modulation transfer function of an imaging system. These methods, apparatuses, and computer program products may provide several advantages to imaging systems, users of imaging systems, as well as technicians responsible for calibrating imaging systems. More particularly, some example embodiments provide for measurement of a modulation transfer function of an imaging system based on a circular shaped feature that may be captured in an image by the imaging system. In this regard, in some example embodiments, the MTF of an imaging system may be measured quantitatively based on a circular feature rather than having to rely on a slanted-edge. Such example embodiments may be advantageous, as slanted-edge measurement may not always be an option since a phantom containing a suitable slanted-edge feature may not be available. Further, the orientation and positioning of a slanted edge (e.g., with respect to horizontal and/or vertical axes) limits the MTF measurement to be obtained only for a specific direction perpendicular to the slanted edge direction, whereas measurement of MTF on the basis of a circular feature in accordance with some example embodiments may be direction invariant.

In a first example embodiment, a method for determining a modulation transfer function of an imaging system is provided. The method of this example embodiment may comprise accessing an image of a phantom having a substantially circular shaped feature captured by the imaging system. The method of this example embodiment may further comprise detecting the circular shaped feature within the image. The method of this example embodiment may additionally comprise defining at least one line extending from a point within the detected circular shaped feature to a point outside of the circular shaped feature. The method of this example embodiment may also comprise determining an edge spread function based at least in part on the defined at least one line. The method of this example embodiment may further comprise determining the modulation transfer function of the imaging system based at least in part on the determined edge spread function.

In another example embodiment, an apparatus for determining a modulation transfer function of an imaging system is provided. The apparatus of this example embodiment comprises at least one processor. The at least one processor may be configured to cause the apparatus of this example embodiment to at least access an image of a phantom having a substantially circular shaped feature captured by the imaging system. The at least one processor may be further configured to cause the apparatus of this example embodiment to detect the circular shaped feature within the image. The at least one processor may be additionally configured to cause the apparatus of this example embodiment to define at least one line extending from a point within the detected circular shaped feature to a point outside of the circular shaped feature. The at least one processor may also be configured to cause the apparatus of this example embodiment to determine an edge spread function based at least in part on the defined at least one line. The at least one processor may be further configured to cause the apparatus of this example embodiment to determine the modulation transfer function of the imaging system based at least in part on the determined edge spread function.

In a further example embodiment, a computer program product for determining a modulation transfer function of an imaging system is provided. The computer program product of this embodiment includes at least one non-transitory computer-readable storage medium having computer-readable program instructions stored therein. The program instructions of this example embodiment may comprise program instructions configured to access an image of a phantom having a substantially circular shaped feature captured by the imaging system. The program instructions of this example embodiment may further comprise program instructions configured to detect the circular shaped feature within the image. The program instructions of this example embodiment may additionally comprise program instructions configured to define at least one line extending from a point within the detected circular shaped feature to a point outside of the circular shaped feature. The program instructions of this example embodiment may also comprise program instructions configured to determine an edge spread function based at least in part on the defined at least one line. The program instructions of this example embodiment may further comprise program instructions configured to determine the modulation transfer function of the imaging system based at least in part on the determined edge spread function.

In yet another example embodiment, an apparatus for determining a modulation transfer function of an imaging system is provided. The apparatus of this example embodiment may comprise means for accessing an image of a phantom having a substantially circular shaped feature captured by the imaging system. The apparatus of this example embodiment may further comprise means for detecting the circular shaped feature within the image. The apparatus of this example embodiment may additionally comprise means for defining at least one line extending from a point within the detected circular shaped feature to a point outside of the circular shaped feature. The apparatus of this example embodiment may also comprise means for determining an edge spread function based at least in part on the defined at least one line. The apparatus of this example embodiment may further comprise means for determining the modulation transfer function of the imaging system based at least in part on the determined edge spread function.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the invention in any way. It will be appreciated that the scope of the invention encompasses many potential embodiments, some of which will be further described below, in addition to those here summarized.

BRIEF DESCRIPTION OF THE DRAWINGS

Figure 1:
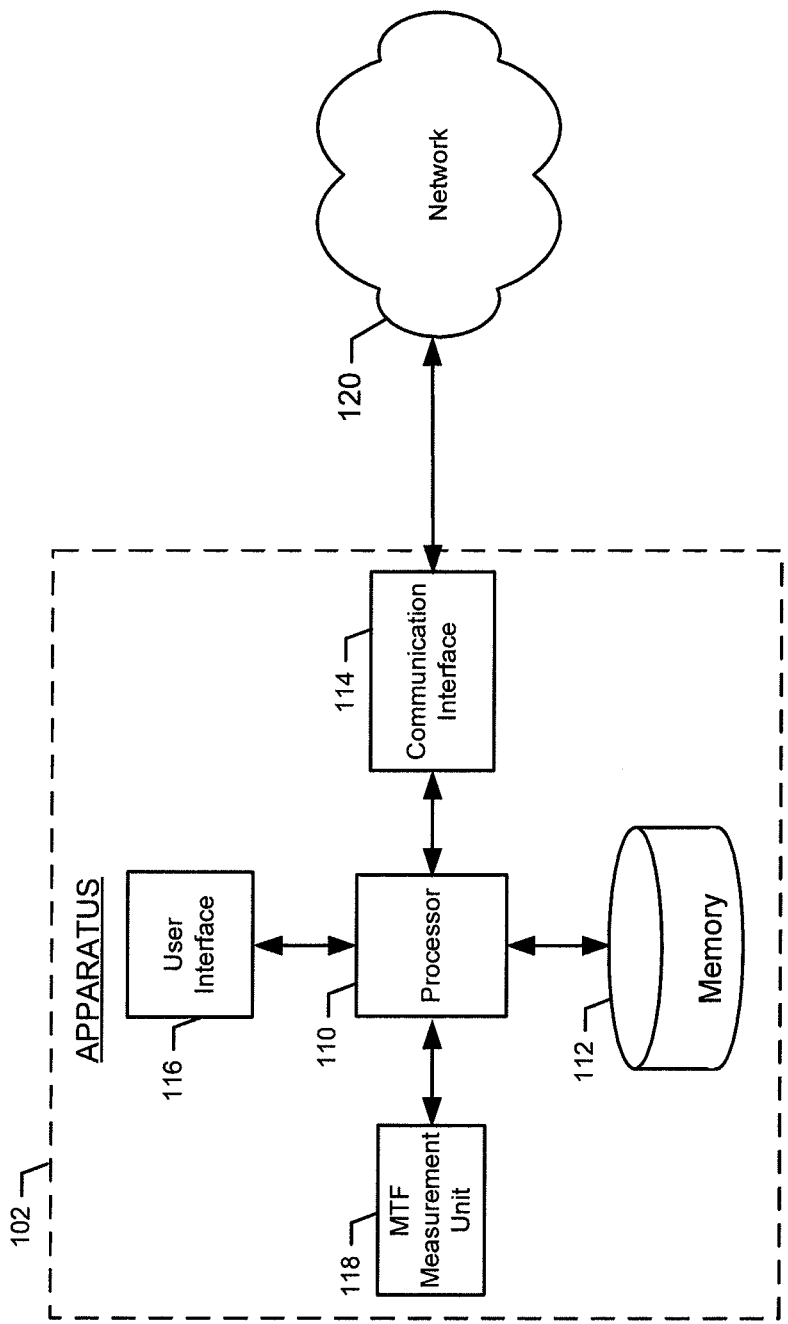
Figure 3:
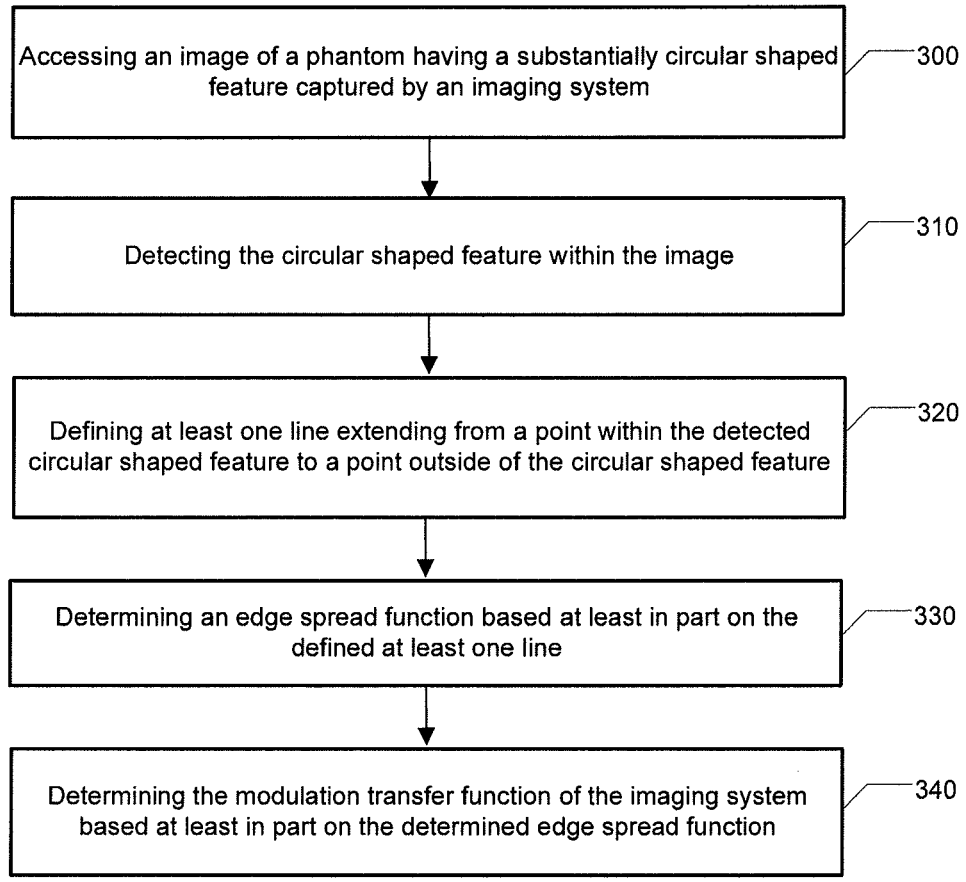
Figure 4:
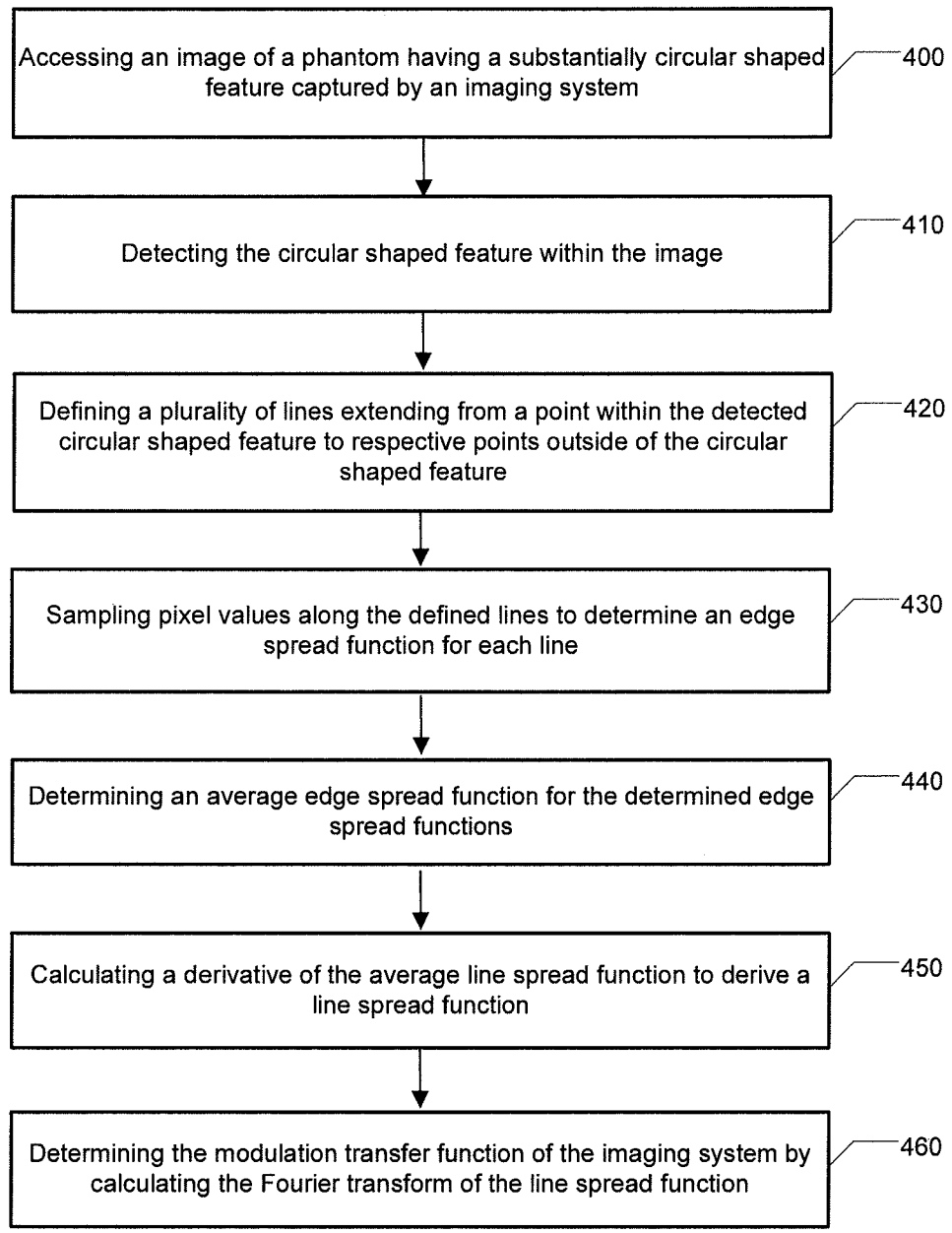

Having thus described embodiments of the invention in general terms, reference will now be made to the accompanying drawings, which are not necessarily drawn to scale, and wherein:

FIG. 1 illustrates a block diagram of an apparatus for determining the modulation transfer function of an imaging system according to some example embodiments;

FIGS. 2A-2I illustrate a procedure for determining the modulation transfer function of an imaging system according to some example embodiments;

FIG. 3 illustrates a flowchart according to an example method for determining the modulation transfer function of an imaging system according to some example embodiments; and FIG. 4 illustrates a flowchart according to another example method for determining the modulation transfer function of an imaging system according to some example embodiments.

DETAILED DESCRIPTION

Some embodiments of the present invention will now be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like reference numerals refer to like elements throughout.

As used herein, the terms "data," "content," "information" and similar terms may be used interchangeably to refer to data capable of being transmitted, received, displayed and/or stored in accordance with various example embodiments. Thus, use of any such terms should not be taken to limit the spirit and scope of the disclosure. Further, where a computing device is described herein to receive data from another computing device, it will be appreciated that the data may be received directly from the another computing device or may be received indirectly via one or more intermediary computing devices, such as, for example, one or more servers, relays, routers, network access points, and/or the like.

FIG. 1 illustrates a block diagram of an apparatus 102 for determining the modulation transfer function of an imaging system according to some example embodiments. It will be appreciated that the apparatus 102 as well as the illustrations in other figures are each provided as an example of some embodiments and should not be construed to narrow the scope or spirit of the disclosure in any way. In this regard, the scope of the disclosure encompasses many potential embodiments in addition to those illustrated and described herein. As such, while FIG. 1 illustrates one example of a configuration of an apparatus for determining the modulation transfer function of an imaging system, numerous other configurations may also be used to implement embodiments of the present invention.

The apparatus 102 may be embodied as any computing device or combination of a plurality of computing devices configured to analyze an image captured by an imaging system to determine the MTF of the imaging system in accordance with one or more example embodiments. In this regard, by way of non-limiting example, the apparatus 102 may be embodied as one or more desktop computers, one or more laptop computers, one or more workstations, one or more network nodes, one or more servers, a server cluster, a cloud computing infrastructure, multiple computing devices in communication with each other, an entity(ies) of a Picture Archiving and Communication System (PACS), any combination thereof, and/or the like. In some example embodiments, the apparatus 102 may be implemented on an imaging system so as to provide self-assessment of the MTF of the imaging system. Alternatively, in some example embodiments, the apparatus 102 may comprise an entity embodied separately from an imaging system that may be configured to receive or otherwise acquire an image captured by the separate imaging system.

In some example embodiments the apparatus 102 includes various means for performing the various functions described herein. These means may include, for example, one or more of a processor 110, memory 112, communication interface 114, user interface 116, or MTF measurement unit 118 for performing the various functions herein described. The means of the apparatus 102 as described herein may be embodied as, for example, circuitry, hardware elements (e.g., a suitably programmed processor, combinational logic circuit, and/or the like), a computer program product comprising a computer-readable medium (e.g. memory 112) storing computer-readable program instructions (e.g., software or firmware) that are executable by a suitably configured processing device (e.g., the processor 110), or some combination thereof.

The processor 110 may, for example, be embodied as various means including one or more microprocessors, one or more coprocessors, one or more multi-core processors, one or more controllers, processing circuitry, one or more computers, various other processing elements including integrated circuits such as, for example, an ASIC (application specific integrated circuit) or FPGA (field programmable gate array), or some combination thereof. Accordingly, although illustrated in FIG. 1 as a single processor, in some embodiments the processor 110 may comprise a plurality of processors. The plurality of processors may be embodied on a single computing device or may be distributed across a plurality of computing devices collectively configured to function as the apparatus 102. The plurality of processors may be in operative communication with each other and may be collectively configured to perform one or more functionalities of the apparatus 102 as described herein. In some embodiments, the processor 110 may be configured to execute instructions stored in the memory 112 or otherwise accessible to the processor 110. These instructions, when executed by the processor 110, may cause the apparatus 102 to perform one or more of the functionalities of the apparatus 102 as described herein. As such, whether configured by hardware or software methods, or by a combination thereof, the processor 110 may comprise an entity capable of performing operations according to embodiments of the present invention while configured accordingly. Thus, for example, when the processor 110 is embodied as an ASIC, FPGA or the like, the processor 110 may comprise specifically configured hardware for conducting one or more operations described herein. Alternatively, as another example, when the processor 110 is embodied as an executor of instructions, such as may be stored in the memory 112, the instructions may specifically configure the processor 110 to perform one or more algorithms and operations described herein.

The memory 112 may include, for example, volatile and/or non-volatile memory. Although illustrated in FIG. 1 as a single memory, the memory 112 may comprise a plurality of memories. The plurality of memories may be embodied on a single computing device or distributed across a plurality of computing devices. The memory 112 may comprise, for example, a hard disk, random access memory, cache memory, flash memory, an optical disc (e.g., a compact disc read only memory (CD-ROM), digital versatile disc read only memory (DVD-ROM), or the like), circuitry configured to store information, or some combination thereof. In this regard, the memory 112 may comprise any non-transitory computer readable storage medium. The memory 112 may be configured to store information, data, applications, instructions, and/or the like for enabling the apparatus 102 to carry out various functions in accordance with example embodiments of the present invention. For example, in some example embodiments, the memory 112 is configured to buffer input data for processing by the processor 110. Additionally or alternatively, in some example embodiments, the memory 112 is configured to store program instructions for execution by the processor 110. The memory 112 may store information in the form of static and/or dynamic information. This stored information may be stored and/or used by the MTF measurement unit 118 during the course of performing its functionalities.

In some example embodiments, the apparatus 102 may include a communication interface(s), such as the communication interface 114. In embodiments including a communication interface, the communication interface 114 may be embodied as any device or means embodied in circuitry, hardware, a computer program product comprising a computer readable medium (e.g., the memory 112) storing computer readable program instructions executed by a processing device (e.g., the processor 110), or a combination thereof that is configured to receive and/or transmit data from/to another device with which the apparatus 102 may be in communication. In some example embodiments, the communication interface 114 is at least partially embodied as or otherwise controlled by the processor 110. In this regard, the communication interface 114 may be in communication with the processor 110, such as via a bus. The communication interface 114 may additionally be in communication with the memory 112, user interface 116, and/or MTF measurement unit 118, such as via a bus. The communication interface 114 may include, for example, an antenna, a transmitter, a receiver, a transceiver and/or supporting hardware or software for enabling communications with another computing device. The communication interface 114 may be configured to receive and/or transmit data using any protocol that may be used for communications between computing devices. As an example, the communication interface 114 may be configured to receive and/or transmit data using any protocol and/or communications technology that may be used for communicating over a network, such as the network 120. The network 120 may comprise one or more wireless networks (e.g., a cellular network, wireless local area network, wireless metropolitan area network, and/or the like), one or more wireline networks (e.g., a wired local area network), or some combination thereof, and in some embodiments comprises at least a portion of the internet.

In some example embodiments, the apparatus 102 may include a user interface, such as the user interface 116. The user interface 116 may be in communication with the processor 110 to receive an indication of a user input and/or to provide an audible, visual, mechanical, or other output to a user. As such, the user interface 116 may include, for example, a keyboard, a mouse, a joystick, a display, a touch screen display, a microphone, a speaker, and/or other input/output mechanisms. The user interface 116 may be in communication with the memory 112, communication interface 114, and/or MTF measurement unit 118, such as via a bus.

The MTF measurement unit 118 may be embodied as various means, such as circuitry, hardware, a computer program product comprising a computer readable medium (e.g., the memory 112) storing computer readable program instructions executed by a processing device (e.g., the processor 110), or some combination thereof and, in some example embodiments, is embodied as or otherwise controlled by the processor 110. In embodiments wherein the MTF measurement unit 118 is embodied separately from the processor 110, the MTF measurement unit 118 may be in communication with the processor 110. The MTF measurement unit 118 may further be in communication with one or more of the memory 112, communication interface 114, or user interface 116, such as via a bus.

In some example embodiments, the MTF measurement unit 118 may be configured to access an image captured by an imaging system in order to analyze the image to determine the MTF of the imaging system. In accessing the image, the MTF measurement unit 118 may, for example, be configured to access an image that may be stored locally, such as in the memory 112. As another example, the MTF measurement unit 118 may access an image by receiving and/or retrieving the image from another device, such as an imaging system, a PACS (Picture Archiving and Communication System), or the like, that may be accessible over the network 120.

The imaging system that captured the image may comprise any imaging system for which an MTF may be measured. For example, the imaging system may comprise an optical device, digital camera, a satellite imaging system, a medical imaging system, and/or other system capable of capturing an image of an object. In embodiments wherein the imaging system comprises a medical imaging system, the imaging system may comprise a magnetic resonance (MR) imaging system, a computed tomography (CT) imaging system, a computed radiography (CR) imaging system, a direct radiography (DR) imaging system, a Mammography (MG) imaging system, or any other imaging modality that may capture digital images.

It will be appreciated however, that the imaging system which may have captured an image that may be accessed by the MTF measurement unit 118 is not limited to embodiment as a physical imaging system. In this regard, the imaging system may comprise a software system, image processing algorithm, and/or the like that may modify or otherwise process a previously captured image. An MTF may accordingly be determined for such a system or algorithm in accordance with some example embodiments in order to quantify any detail loss that may be associated with application of the imaging system (e.g., the image processing software or algorithm) to the image. As such, it will be appreciated that unless otherwise noted, where determination of an MTF for an imaging system that captured an image is described herein, the imaging system referred to as having captured the image may comprise a physical imaging system that may have captured the image, an image processing system or algorithm that may have captured (e.g., generated) the image by processing or otherwise modifying another image, some combination thereof, or the like.

A phantom captured in an accessed image may comprise any object which may be captured in an imaging system having a substantially circular shaped feature(s) that may enable determination of the MTF of the imaging system in accordance with one or more example embodiments. In some example embodiments, the phantom may comprise an American College of Radiology Computed Tomography Accreditation phantom, such as the Gammex® 464 or the like, which may include one or more circular shaped features.

The MTF measurement unit 118 may be configured to detect the circular shaped feature(s) within an image. For example, in some example embodiments, the MTF measurement unit 118 may be configured to analyze the image and automatically detect the substantially circular shaped feature(s) within the image. In this regard, The MTF measurement unit 118 may be configured to apply any appropriate image feature extraction technique, computer vision technique, or the like in order to detect a circular shaped feature. For example, in some example embodiments, the MTF measurement unit 118 may be configured to apply an edge detection technique, such as, for example, a Canny edge detector, to the image to detect the edges in the image and use the detected edges to detect the circular shaped feature(s) within the image. In order to facilitate edge detection in the image, the MTF measurement unit 118 may be configured to transform the image into a gradient image and detect the edges based upon the gradient image. The MTF measurement unit 118 may analyze the detected edges to identify the circular shaped region(s). For example, a Hough transform and/or other technique may be applied to the detected edges so as to identify the circular shaped region(s).

In some example embodiments, the MTF measurement unit 118 may be configured to detect the circular shaped feature(s) within an image with the assistance of a user. In this regard, a user may view the image and provide an indication of the circular feature. As an example, a user may select a region of the image including the circular shaped feature, select one or more edge points on the arc of the circular shaped feature, and/or the like. The MTF measurement unit 118 may detect the circular shaped feature on the basis of the user input.

The MTF measurement unit 118 may be further configured to define one or more lines (e.g., sampling lines). Each respective sampling line may extend from a point within a detected circular shaped feature to a point outside of the circular shaped feature. If multiple lines are defined, the point of origin of two or more respective lines within the circular shaped feature may be a common point, such as the center point of the circular shaped feature, or may differ such that two respective lines may originate from two different points within the circular shaped feature. If multiple lines are defined, the directions of the lines may be offset from one another such that lines may cross different points (e.g., edges) along the arc of the circular shaped feature. The offset between each defined line may, for example, be a constant number of degrees. Accordingly, for example, if 32 lines are defined with equal offsets, then the orientation of each defined line may be rotated 11.25 degrees from the orientation of another line (e.g., an adjacent line). Alternatively, the offset between defined lines may vary such that the offset between a first pair of lines may differ from the offset between a second pair of lines. In some embodiments wherein multiple lines are defined, a line having a fixed origin point within the circular shaped feature may be rotated around (e.g., clockwise or counterclockwise) the circular shaped feature in a series of steps by an offset amount, thereby defining a sampling line at each rotation step. The length of the defined lines may comprise any length so long as the length of a respective line is sufficient to extend from a point of origin within the circular shaped feature to a point outside of the circular shaped feature.

In some example embodiments, the defined line(s) may comprise radial lines extending from the center point of the circular shaped feature and extending outward for a length greater than the radius of the circular shaped feature. As an example, the length of the lines may be twice the length of the radius of the circular shaped feature. However, it will be appreciated that the line length in some example embodiments using radial lines extending from the center point may be any length that is greater than the radius of the circular shaped feature. In embodiments wherein the MTF measurement unit 118 uses a Hough transform to detect the circular shaped feature, the center point and radius of the circular shaped feature may already be known to the MTF measurement unit 118, and may be used to define the radial lines. If, however, the center point and radius of the circular shaped feature is not known from analysis used to detect the circular shaped feature, the MTF measurement unit 118 may be configured in some example embodiments to determine the center point and radius length and use these values to facilitate defining one or more radial lines.

In some example embodiments, defining the line(s) may comprise a user-assisted process whereby a user may provide input based upon which the MTF measurement unit may define a line. In this regard, a user may select a starting point, end point, orientation, length of a line, and/or other parameters via the user interface 116. For example, some example embodiments may provide a graphical user interface by which a user may draw a line over a portion of the circular shaped feature, select starting and/or ending points for a line, and/or the like.

The MTF measurement unit 118 may be further configured to use the pixel values along the defined line(s) to determine an edge spread function in order to facilitate measurement of the MTF of the imaging system that captured the image. In this regard, the MTF measurement unit 118 may sample the pixels along a line to determine an edge spread function. Accordingly, the defined line(s) may be considered "sampling lines." It will be appreciated that the sampling rate at which pixels along a line may be sampled may vary in various example embodiments. However, by way of example, in some example embodiments, pixels along a line may be sampled at a sampling rate three (3) times the pixel size. Sampling of a line may, for example, proceed from a point of origin of the line within the circular shaped feature to a point of termination of the line outside of the circular shaped feature. The MTF measurement unit 118 may accordingly be configured to use a line(s) extending from a point within a circular shaped feature to a point outside of the circular shaped feature to measure an edge spread function on the edges of the circular shaped feature.

In embodiments wherein multiple sampling lines are defined, the MTF measurement unit 118 may be configured to determine an edge spread function for each of the sampling lines and determine an average edge spread function for the determined edge spread functions. The MTF measurement unit 118 may use the average edge spread function as the basis for determining the MTF of the imaging system.

If the sampling lines comprise radial lines originating from the center of the circular shaped feature, the MTF measurement unit 118 may determine the average edge spread function by adding the edge spread functions together and dividing the summed edge spread functions by the number of edge spread functions (e.g., the number of sampling lines).

If, however, one or more of the sampling lines originate from a point other than the center of the circular shaped feature, the MTF measurement unit 118 may align the edge spread functions in order to determine the average edge spread function. In order to align the edge spread functions, the MTF measurement unit 118 may determine the center point of each edge spread function and use the determined center points to align the edge spread functions. The MTF measurement unit 118 may use the average value of pixels in a region of the image inside of the circular shaped feature (AVGin) and an average value of pixels in a region of the image outside of the circular shaped feature (AVGout) to determine the center point of an edge spread function. In this regard, the center point of an edge spread function may be defined as a point having a pixel value of approximately (AVGin−AVGout)/2. The regions inside and outside of the circular shaped feature for which AVGin and AVGout may, for example, be defined to be at least a threshold distance (e.g., at least a threshold number of pixels) away from the edges of the circular shaped feature. The regions may be automatically determined by the MTF measurement unit 118, or may be defined as regions of interest by a user. The MTF measurement unit 118 may determine the average edge spread function by adding the aligned edge spread functions together and dividing the summed edge spread functions by the number of edge spread functions (e.g., the number of sampling lines).

In some example embodiments, the MTF measurement unit 118 may be configured to derive a line spread function, which may be used to determine the MTF, from the edge spread function (e.g., the average edge spread function in some example embodiments wherein multiple sampling lines are used) by calculating a derivative of the edge spread function. In some instances in which multiple sampling lines are used, rather than determining a line spread function from an average edge spread function, an intermediate line spread function may be determined for each respective edge spread function. An average line spread function, which may be used to determine the MTF, may be determined for the intermediate line spread functions. As such, it will be appreciated that a line spread function used to determine the MTF of the imaging system in instances in which multiple sampling lines are used may, for example, be derived by determining a derivative of an average edge spread function for the sampling lines, or may comprise an average of a plurality of intermediate line spread functions.

The MTF measurement unit 118 may use the line spread function to determine the MTF of the imaging system. In this regard, the MTF measurement unit 118 may, for example, be configured to determine the MTF by calculating the modulus of the discrete Fourier transform of the line spread function.

In some example embodiments, the MTF measurement unit 118 may be configured to modify the determined MTF to conform to a desired output format. For example, the MTF measurement unit 118 may normalize the MTF, such as by normalizing the MTF to have a value of 1 or 100% at an initial (e.g., 0) frequency (1 p/mm or mm$^{-1}$).

The MTF measurement unit 118 may be further configured to cause output of the determined MTF. For example, the MTF may be displayed on a display that may be included in the user interface 116. As another example, the MTF may be sent to a recipient, such as via email. As a further example, the MTF may be output to a database or file, which may, for example, be used for quality assurance purpose (e.g., tracking of MTF values over time). In addition, certain metrics based on MTF curve, such as the area under MTF or the frequency at which MTF decreases to 10% level, may be extracted, recorded, and once beyond certain threshold values, an automated notification may be provided, such as via email. It will be appreciated that these modes of output are provided by way of example, and not by way of limitation, as a determined MTF may be output by way of any available mode.

In some example embodiments, the MTF determined for an imaging system may be used to calibrate the imaging system. In some example embodiments wherein the apparatus 102 is embodied on and/or otherwise in operative communication with the imaging system, calibration of the imaging system may, for example, be performed by and/or at the direction of the MTF measurement unit 118.

Figure 2A:
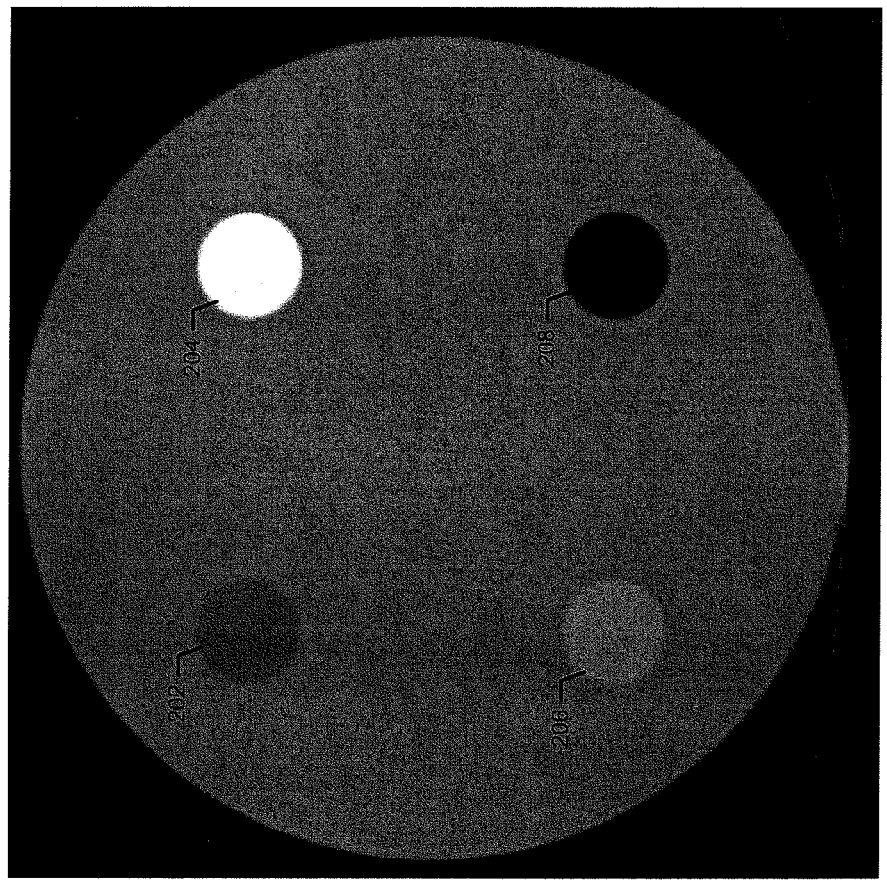

FIGS. 2A-2I illustrate a procedure for determining the modulation transfer function of an imaging system according to some example embodiments. FIG. 2A illustrates an example image of an example phantom that may be captured by an imaging system. The phantom may, for example, comprise an American College of Radiology Computed Tomography Accreditation phantom, such as the Gammex® 464. As may be seen from FIG. 2A, the phantom, itself, has a circular shape, which may be used to determine the MTF of the imaging system that captured the image. In addition, the illustrated phantom includes substantially circular shaped features 202, 204, 206, and 208, one or more of which may be used to determine the MTF of the imaging system that captured the image.

Figure 2B:
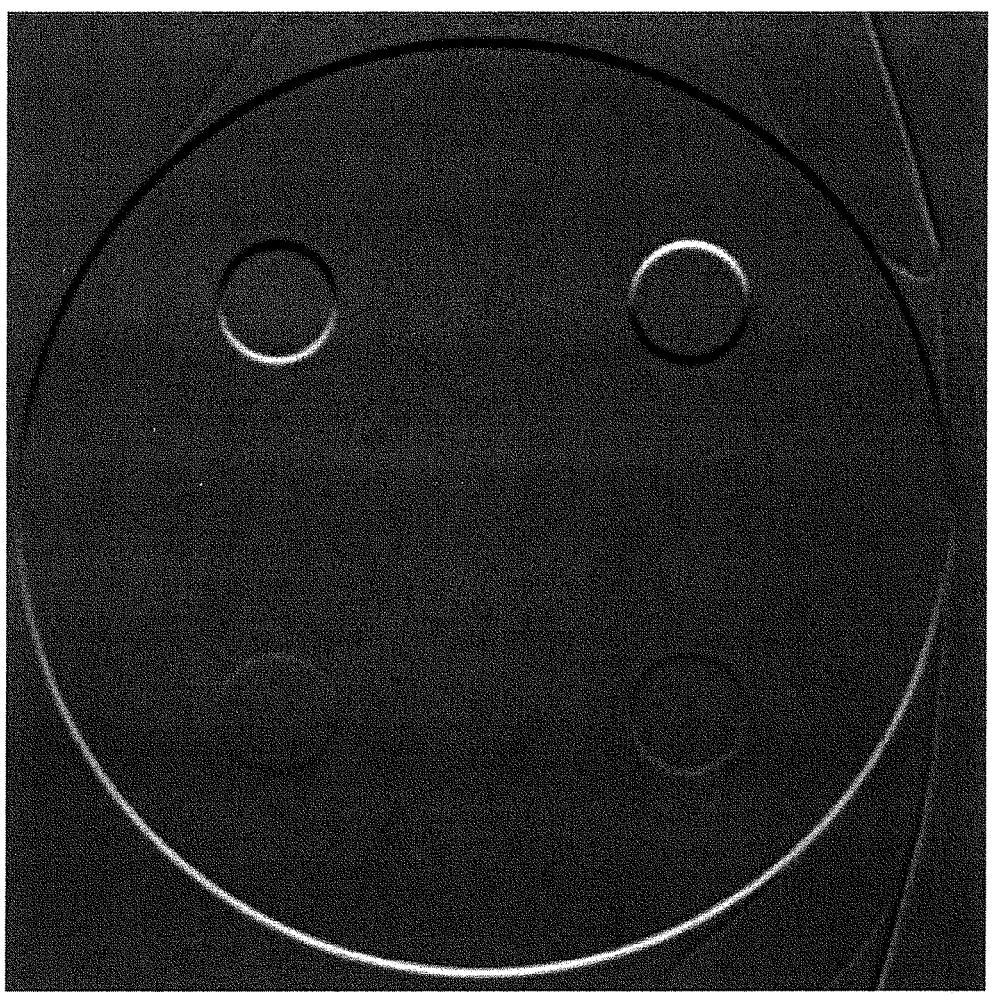
Figure 2C:
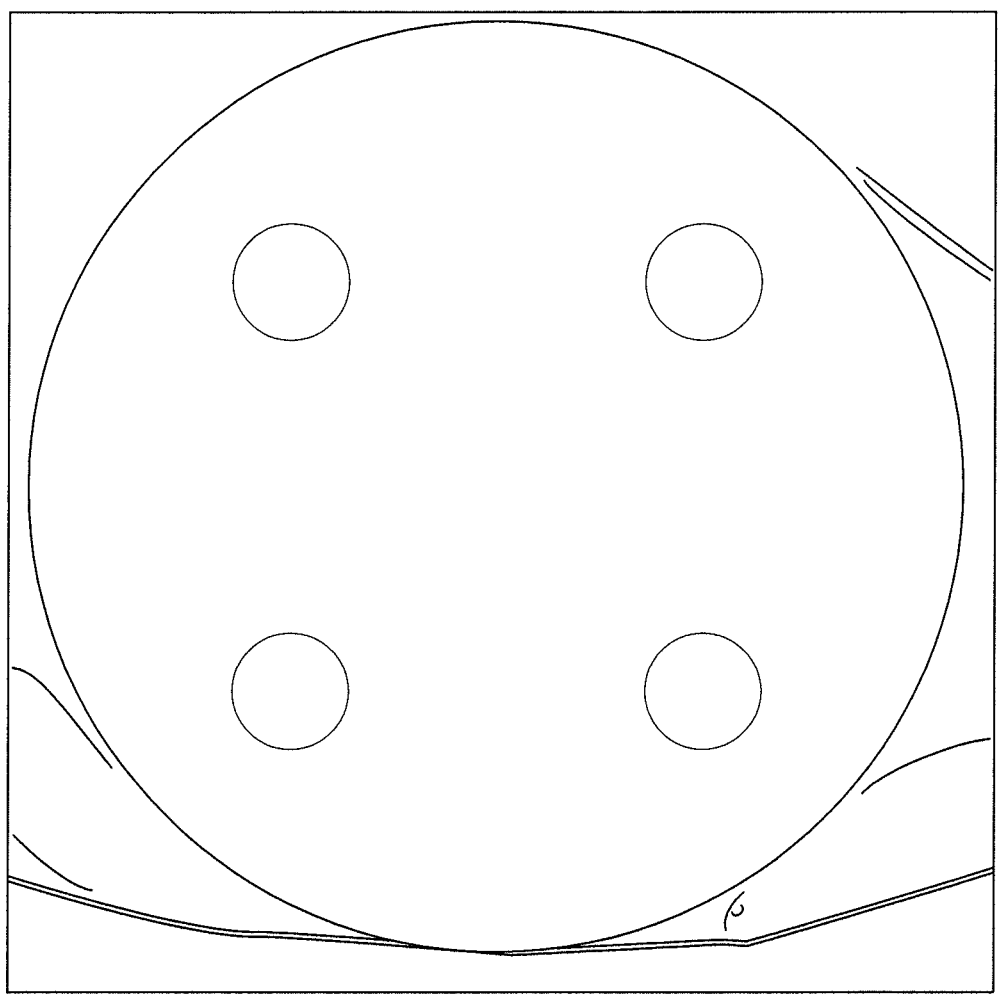
Figure 2D:
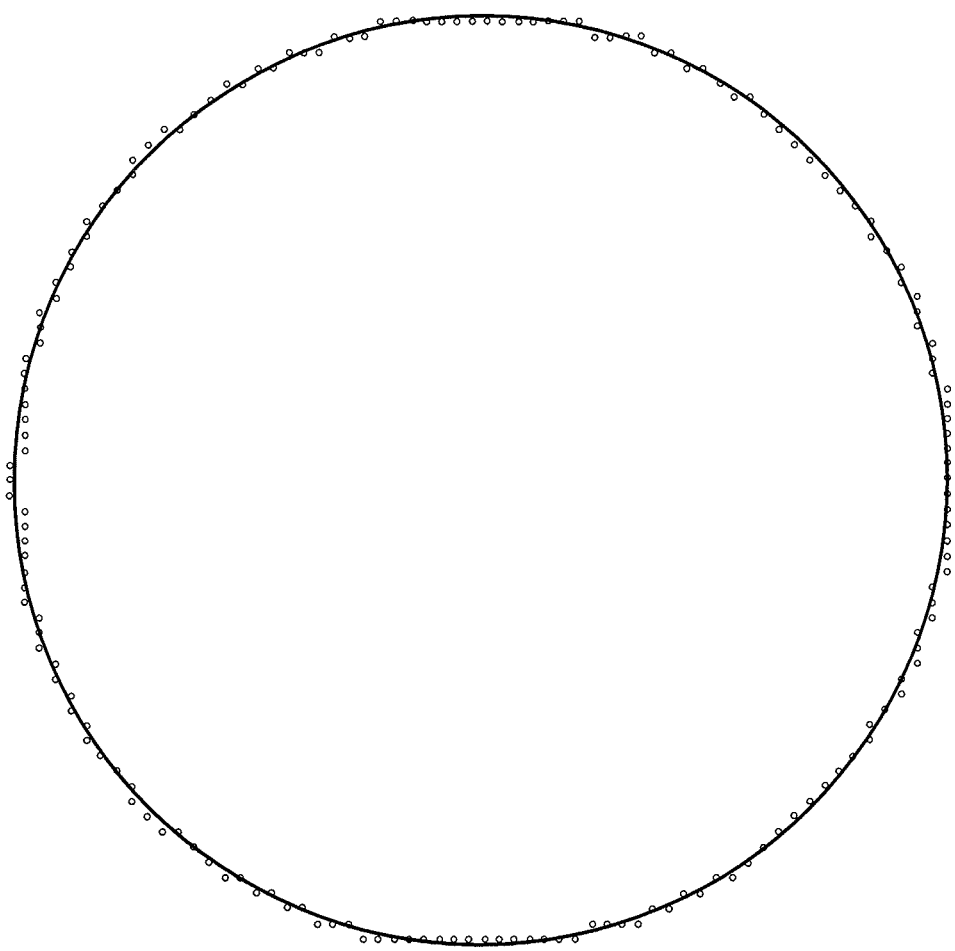
Figure 2E:
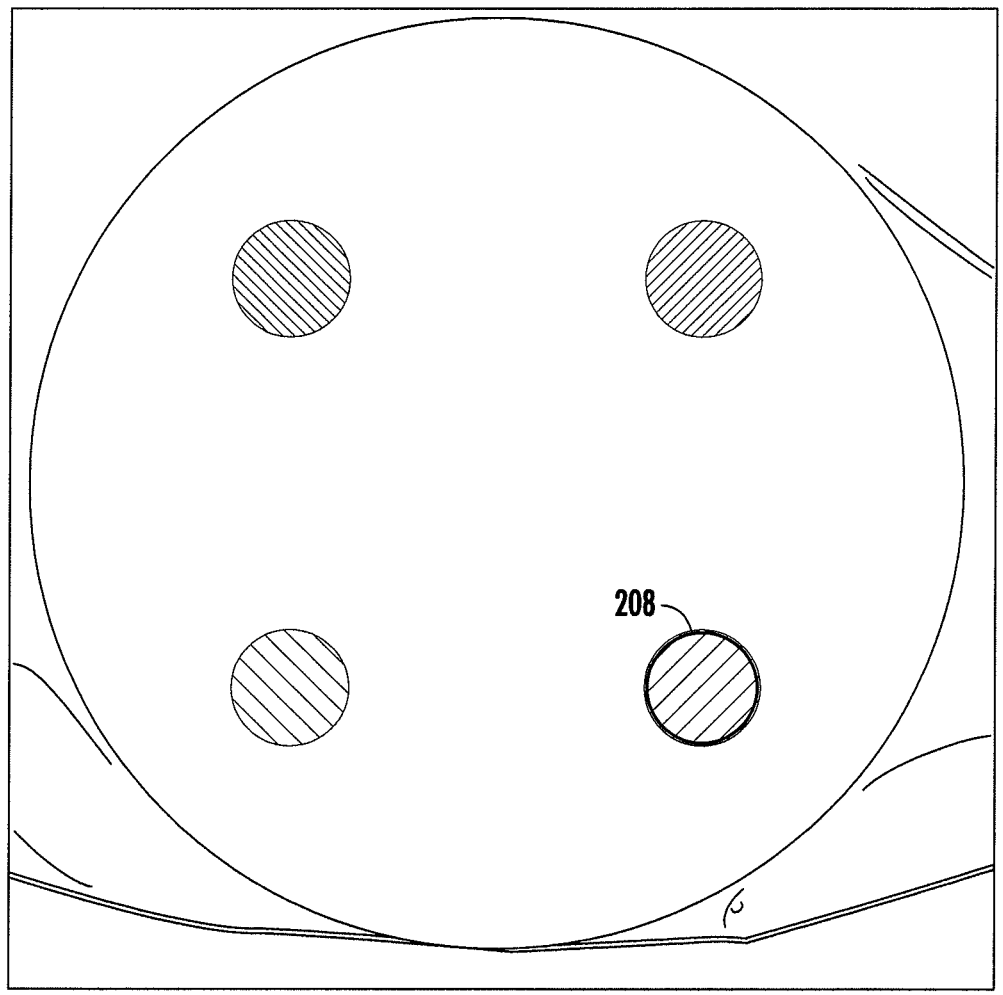

The MTF measurement unit 118 may convert the image of FIG. 2A into the gradient image illustrated in FIG. 2B to facilitate detection of edge points. FIG. 2C illustrates edge points that may be detected by the MTF measurement unit 118 by application of an edge detector, such as a Canny Edge detector, to the gradient image of FIG. 2B. The MTF measurement unit 118 may apply a feature detection technique to the detected edge points in order to detect a circular feature in the image. As an example, the MTF measurement unit 118 may apply a Hough transform to the edge points to fit a circle to one or more regions of the image. FIG. 2D illustrates an example of fitting a circle to edge points that may be detected for the circular shaped feature 208. In FIG. 2E, the circular shaped feature 208 is highlighted, illustrating that the circular shaped feature 208 has been detected based upon the results of the example circle fitting illustrated in FIG. 2D.

Figure 2F:
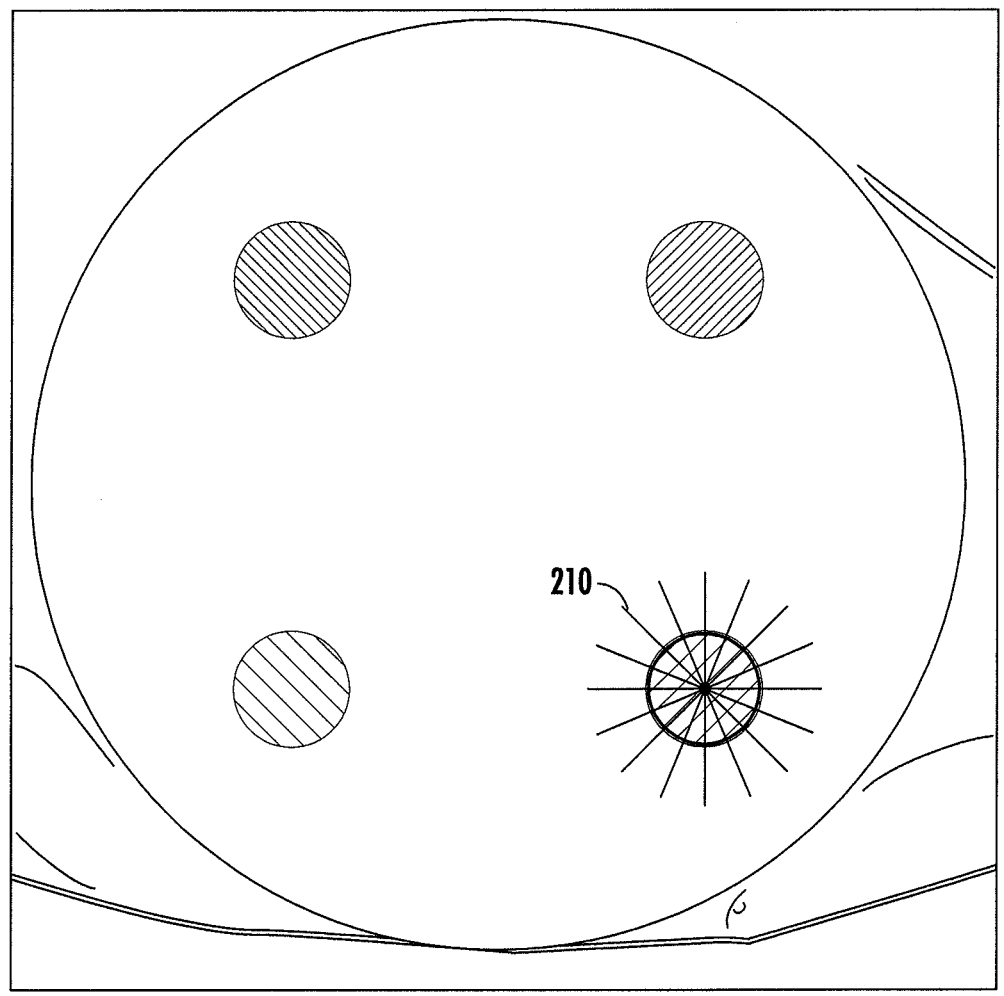

As illustrated in FIG. 2F, the MTF measurement unit 118 may define a plurality of radial lines 210 to the circular shaped feature 208. It will be appreciated that the number of lines illustrated in FIG. 2F and the offset between each line is illustrated merely by way of example, and not by way of limitation. The MTF measurement unit 118 may sample pixel values along the radial lines to determine an edge spread function for each of the radial lines.

Figure 2G:
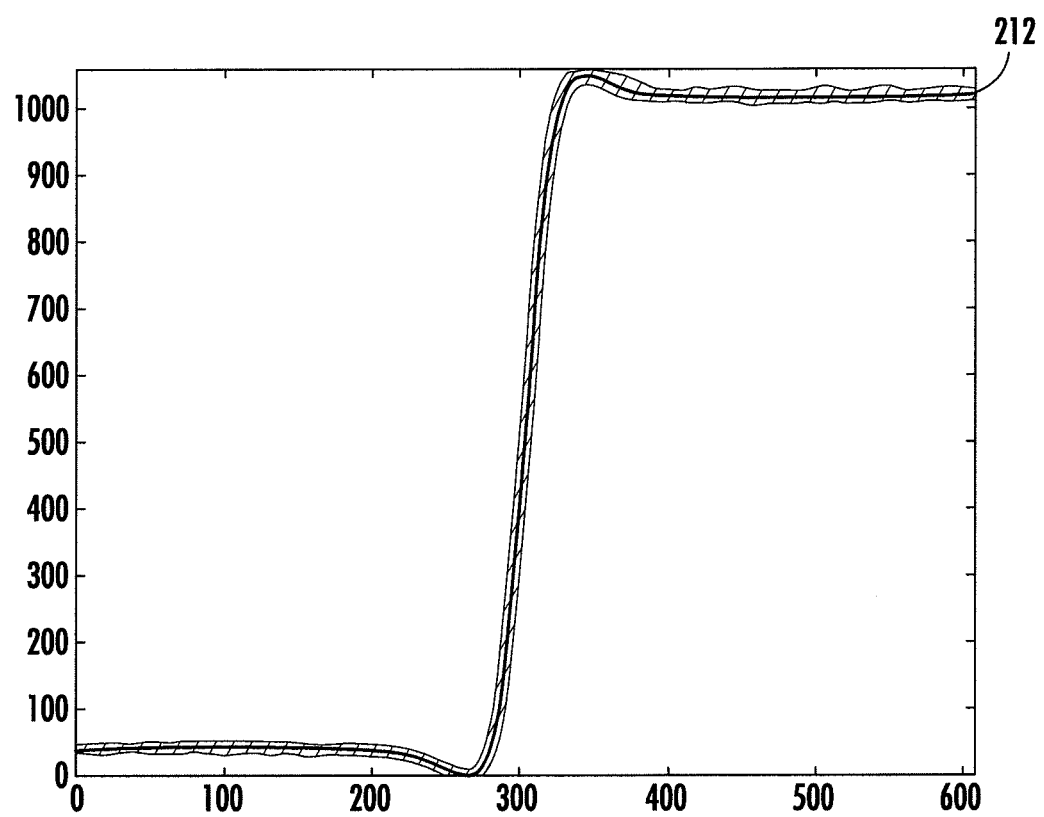
Figure 2H:
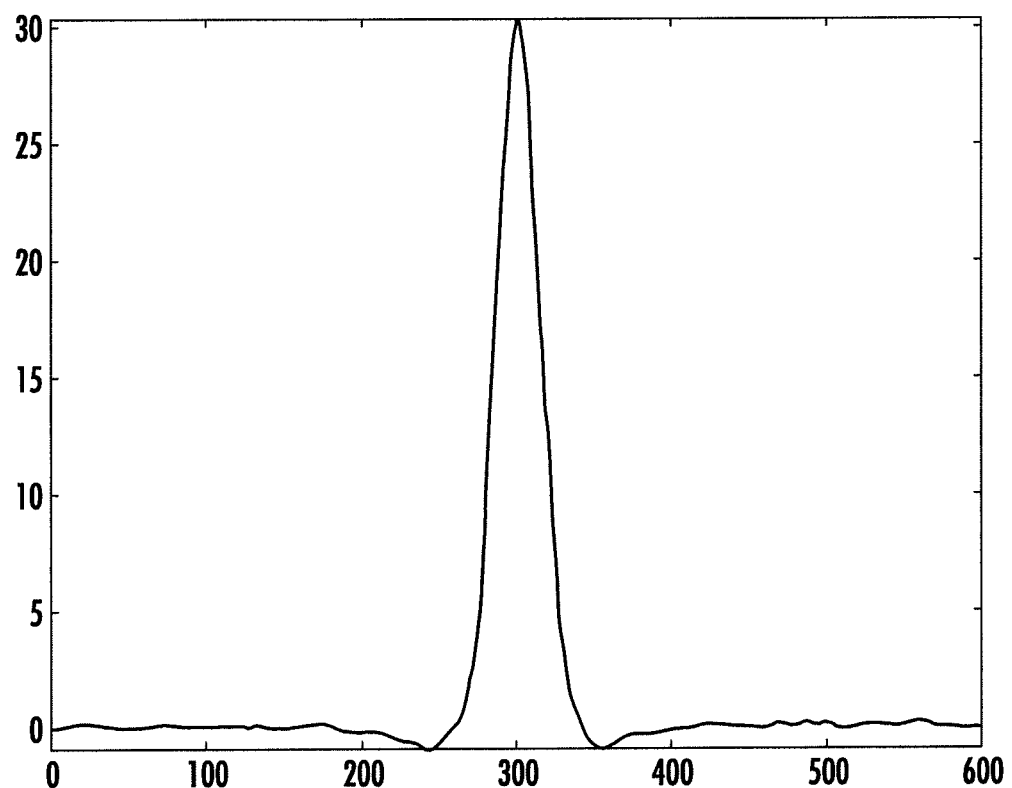
Figure 2I:
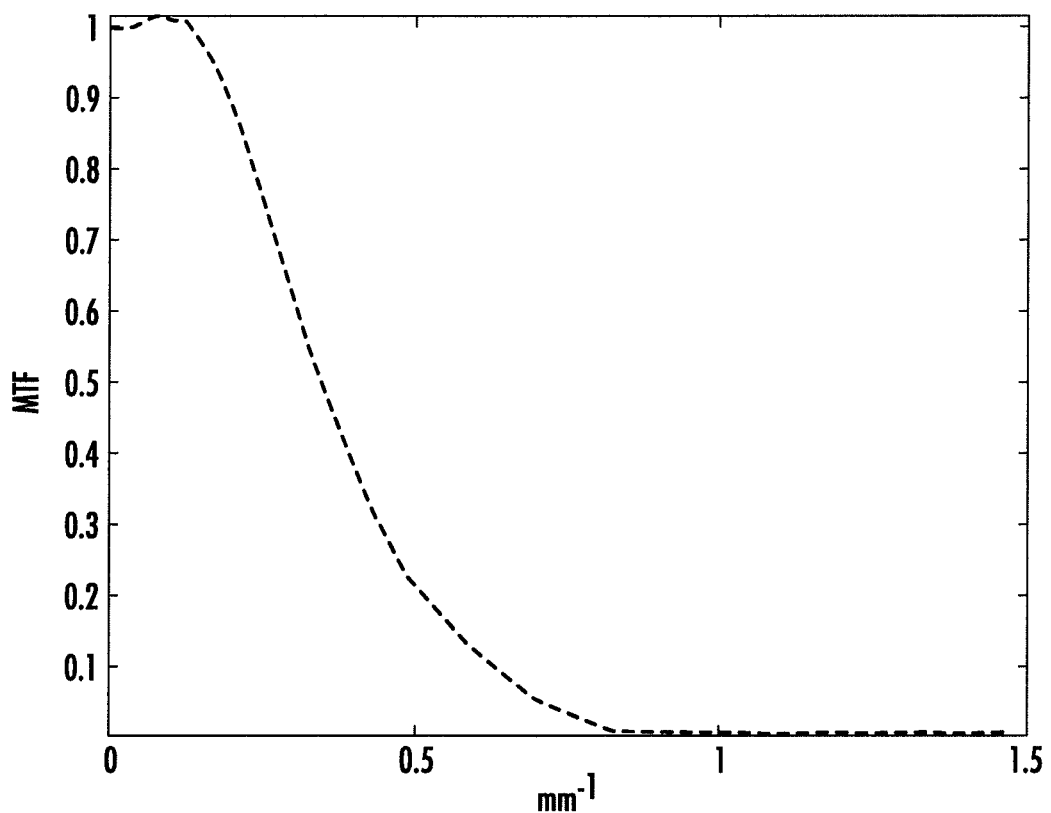

FIG. 2G illustrates a graph of an example result of adding the determined edge spread functions together, with an example average edge spread function illustrated as the line 212 that lies substantially in the center of the Edge spread functions. The horizontal axis in the example of FIG. 2G includes the pixel indices along radial lines 210 and the vertical axis represents the intensity (pixel) values of each pixel indices. Depending on the noise level on the image and selected circular shaped feature like 208, the individual edge spread functions may vary significantly from each other and what is shown here is based on circular object 208 of an image with very high signal to noise ratio and therefore the difference between individual edge spread functions may not be very significant. The MTF measurement unit 118 may determine a line spread function based on the average edge spread function 212 by calculating the derivative of the average edge spread function 212. An example resulting edge spread function is illustrated in FIG. 2H. The MTF measurement unit 118 may determine the MTF of the imaging system that captured the image in FIG. 2A by calculating the modulus of the discrete Fourier transform of the line spread function illustrated in FIG. 2H. An example of an MTF that may be determined is illustrated in FIG. 2I.

Referring now to FIG. 3, FIG. 3 illustrates a flowchart according to an example method for determining the modulation transfer function of an imaging system according to some example embodiments. In this regard, FIG. 3 illustrates a method that may be at least partially performed by an apparatus 102. The operations illustrated in and described with respect to FIG. 3 may, for example, be performed by, with the assistance of, and/or under the control of one or more of the processor 110, memory 112, communication interface 114, user interface 116, or MTF measurement unit 118. Operation 300 may comprise accessing an image of a phantom having a substantially circular shaped feature captured by an imaging system. The processor 110, memory 112, communication interface 114, user interface 116, and/or MTF measurement unit 118 may, for example, provide means for performing operation 300. Operation 310 may comprise detecting the circular shaped feature within the image. The processor 110, memory 112, user interface 116, and/or MTF measurement unit 118 may, for example, provide means for performing operation 310. Operation 320 may comprise defining at least one line extending from a point within the detected circular shaped feature to a point outside of the circular shaped feature. The processor 110, memory 112, user interface 116, and/or MTF measurement unit 118 may, for example, provide means for performing operation 320. Operation 330 may comprise determining an edge spread function based at least in part on the defined at least one line. The processor 110, memory 112, and/or MTF measurement unit 118 may, for example, provide means for performing operation 330. Operation 340 may comprise determining the modulation transfer function of the imaging system based at least in part on the determined edge spread function. The processor 110, memory 112, and/or MTF measurement unit 118 may, for example, provide means for performing operation 340.

FIG. 4 illustrates a flowchart according to another example method for determining the modulation transfer function of an imaging system according to some example embodiments. In this regard, FIG. 4 illustrates a method that may be at least partially performed by an apparatus 102. The operations illustrated in and described with respect to FIG. 4 may, for example, be performed by, with the assistance of, and/or under the control of one or more of the processor 110, memory 112, communication interface 114, user interface 116, or MTF measurement unit 118. Operation 400 may comprise accessing an image of a phantom having a substantially circular shaped feature captured by an imaging system. The processor 110, memory 112, communication interface 114, user interface 116, and/or MTF measurement unit 118 may, for example, provide means for performing operation 400. Operation 410 may comprise detecting the circular shaped feature within the image. The processor 110, memory 112, user interface 116, and/or MTF measurement unit 118 may, for example, provide means for performing operation 410. Operation 420 may comprise defining a plurality of lines extending from a point within the detected circular shaped feature to respective points outside of the circular shaped feature. The processor 110, memory 112, user interface 116, and/or MTF measurement unit 118 may, for example, provide means for performing operation 420. Operation 430 may comprise sampling pixel values along the defined lines to determine an edge spread function for each line. The processor 110, memory 112, and/or MTF measurement unit 118 may, for example, provide means for performing operation 430. Operation 440 may comprise determining an average edge spread function for the edge spread functions determined in operation 430. The processor 110, memory 112, and/or MTF measurement unit 118 may, for example, provide means for performing operation 440. Operation 450 may comprise calculating a derivative of the average edge spread function to derive a line spread function. The processor 110, memory 112, and/or MTF measurement unit 118 may, for example, provide means for performing operation 450. Operation 460 may comprise determining the modulation transfer function of the imaging system by calculating the modulus of the discrete Fourier transform of the line spread function. The processor 110, memory 112, and/or MTF measurement unit 118 may, for example, provide means for performing operation 460.

FIGS. 3-4 each illustrate a flowchart of a system, method, and computer program product according to example embodiments of the invention. It will be understood that each block of the flowcharts, and combinations of blocks in the flowcharts, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices of a server, desktop computer, laptop computer, mobile computer, or other computing device (e.g., an apparatus 102) and executed by a processor (e.g., the processor 110) in the computing device. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s). The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks or steps of the flowcharts support combinations of means for performing the specified functions and combinations of steps for performing the specified functions. It will also be understood that one or more blocks of the flowcharts, and combinations of blocks in the flowcharts, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processor may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method for determining a modulation transfer function of an imaging system, the method comprising:
    accessing an image of a phantom having a circular shaped feature captured by the imaging system;
    detecting the circular shaped feature within the image;
    defining at least one line extending from a point within the detected circular shaped feature to a point outside of the circular shaped feature;
    determining, by a processor, an edge spread function based at least in part on the defined at least one line by at least:
        determining an edge spread function for each defined line; and
        determining an average edge spread function for the determined edge spread functions; and
    determining the modulation transfer function of the imaging system based at least in part on the determined average edge spread function.

2. The method of claim 1, wherein defining the at least one line comprises defining at least one radial line extending from a center point of the circular shaped feature and extending outward for a length greater than a radius of the circular shaped feature.

3. The method of claim 1, wherein determining the edge spread function comprises determining the edge spread function based at least in part on pixel values along the at least one line.

4. The method of claim 1, wherein in an instance in which a plurality of lines are defined and at least one line does not originate from a center point of the circular shaped feature, determining the edge spread function comprises:
    determining a center point for each determined edge spread function based at least in part on an average value of pixels inside the circular shaped feature and on an average value of pixels in a region of the image outside of the circular shaped feature;
    using the determined center points to align the edge spread functions; and
    determining an average edge spread function based on the aligned edge spread functions.

5. The method of claim 1, wherein determining the modulation transfer function of the imaging system based at least in part on the determined edge spread function comprises:
    deriving a line spread function by calculating a derivative of the edge spread function; and
    determining the modulation transfer function by determining the modulus of the discrete Fourier transform of the line spread function.

6. The method of claim 1, wherein detecting the circular shaped feature within the image comprises using a Hough transform to detect the circular shaped feature.

7. The method of claim 1, wherein the phantom comprises an American College of Radiology Computed Tomography Accreditation phantom.

8. The method of claim 1, wherein the imaging system comprises a medical imaging system.

9. An apparatus for determining a modulation transfer function of an imaging system, the apparatus comprising at least one processor, wherein the at least one processor is configured to cause the apparatus to at least:
    access an image of a phantom having a circular shaped feature captured by the imaging system;
    detect the circular shaped feature within the image;
    define at least one line extending from a point within the detected circular shaped feature to a point outside of the circular shaped feature;
    determine an edge spread function based at least in part on the defined at least one line;
    determine an edge spread function for each defined line;
    determine an average edge spread function for the determined edge spread functions; and
    determine the modulation transfer function of the imaging system based at least in part on the determined average edge spread function.

10. The apparatus of claim 9, wherein the at least one processor is further configured to cause the apparatus to define the at least one line at least in part by defining at least one radial line extending from a center point of the circular shaped feature and extending outward for a length greater than a radius of the circular shaped feature.

11. The apparatus of claim 9, wherein the at least one processor is further configured to cause the apparatus to determine the edge spread function based at least in part on pixel values along the at least one line.

12. The apparatus of claim 9, wherein the at least one processor is further configured to cause the apparatus to:
    determine a center point for each determined edge spread function based at least in part on an average value of pixels inside the circular shaped feature and on an average value of pixels in a region of the image outside of the circular shaped feature;
    use the determined center points to align the edge spread functions; and
    determine an average edge spread function based on the aligned edge spread functions.

13. The apparatus of claim 9, wherein the at least one processor is further configured to cause the apparatus to determine the modulation transfer function of the imaging system at least in part by:
deriving a line spread function by calculating a derivative of the edge spread function; and
determining the modulation transfer function by determining the modulus of the discrete Fourier transform of the line spread function.

14. The apparatus of claim 9, wherein the at least one processor is further configured to cause the apparatus to use a Hough transform to detect the circular shaped feature.

15. The apparatus of claim 9, wherein the phantom comprises an American College of Radiology Computed Tomography Accreditation phantom.

16. The apparatus of claim 9, wherein the imaging system comprises a medical imaging system.

17. A computer program product for determining a modulation transfer function of an imaging system, the computer program product comprising at least one non-transitory computer-readable storage medium having computer-readable program instructions stored therein, the computer-readable program instructions comprising:
program instructions configured to access an image of a phantom having a circular shaped feature captured by the imaging system;
program instructions configured to detect the circular shaped feature within the image;
program instructions configured to define at least one line extending from a point within the detected circular shaped feature to a point outside of the circular shaped feature;
program instructions configured to determine an edge spread function based at least in part on the defined at least one line;
program instructions configured to determine an edge spread function for each defined line;
program instructions configured to determine an average edge spread function for the determined edge spread functions; and
program instructions configured to determine the modulation transfer function of the imaging system based at least in part on the determined average edge spread function.

18. The computer program product of claim 17, wherein the program instructions configured to determine the edge spread function comprise:
program instructions configured to determine an average edge spread function for the determined edge spread functions
wherein the program instructions configured to determine the modulation transfer function comprise program instructions configured to determine the modulation transfer function based at least in part on the average edge spread function.

* * * * *